United States Patent [19]

Ko et al.

[11] Patent Number: 4,860,756
[45] Date of Patent: Aug. 29, 1989

[54] ELECTROMAGNETIC BONE HEALING SENSOR USING A MULTI-COIL SENSOR ARRAY

[75] Inventors: Harvey W. Ko; Lynn W. Hart, both of Columbia; Joseph P. Skura, Ellicott City, all of Md.

[73] Assignee: The Johns Hopkins University, Baltimore, Md.

[21] Appl. No.: 89,190

[22] Filed: Aug. 25, 1987

Related U.S. Application Data

[63] Continuation-in-part of Ser. No. 753,824, Jul. 11, 1985, Pat. No. 4,688,580.

[51] Int. Cl.⁴ .............................................. A61B 5/05
[52] U.S. Cl. .................................... 128/653; 128/734; 324/232; 324/237
[58] Field of Search ................................. 128/1.3–1.5, 128/630, 653, 734, 419 F; 324/232, 236, 237

[56] References Cited

U.S. PATENT DOCUMENTS

| | | |
|---|---|---|
| 3,497,799 | 2/1970 | Harmon .............................. 324/237 |
| 3,697,868 | 10/1972 | Carossi et al. ...................... 324/237 |
| 4,234,848 | 11/1980 | Diem et al. .......................... 324/237 |
| 4,467,281 | 8/1984 | Davis et al. .......................... 324/237 |
| 4,574,809 | 3/1986 | Talish et al. ..................... 128/419 F |
| 4,651,093 | 3/1987 | Detricht et al. ..................... 324/232 |

Primary Examiner—Ruth Smith
Attorney, Agent, or Firm—Robert E. Archibald; Howard W. Califano

[57] ABSTRACT

An apparatus and method for non-invasive sensing of bone healing is disclosed. The apparatus and method uses an electromagnetic field to measure impedance changes at and about the bone fracture site during the healing process. The impedance change at the fracture site is a direct indication of the mechanical strength of the fracture site. A multi-coil sensor array is taught, which may be sutured to the patient's skin or mounted onto a plug that is inserted through a window in the cast.

2 Claims, 6 Drawing Sheets

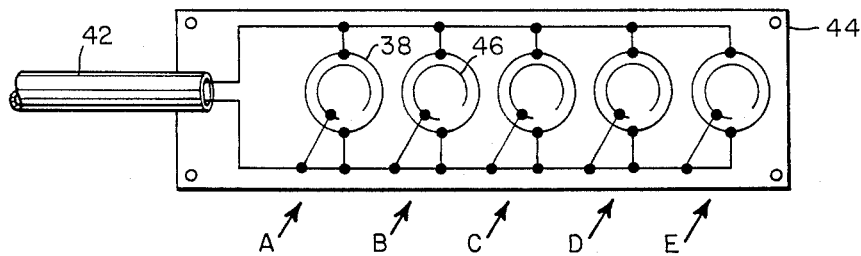
FIG. 9
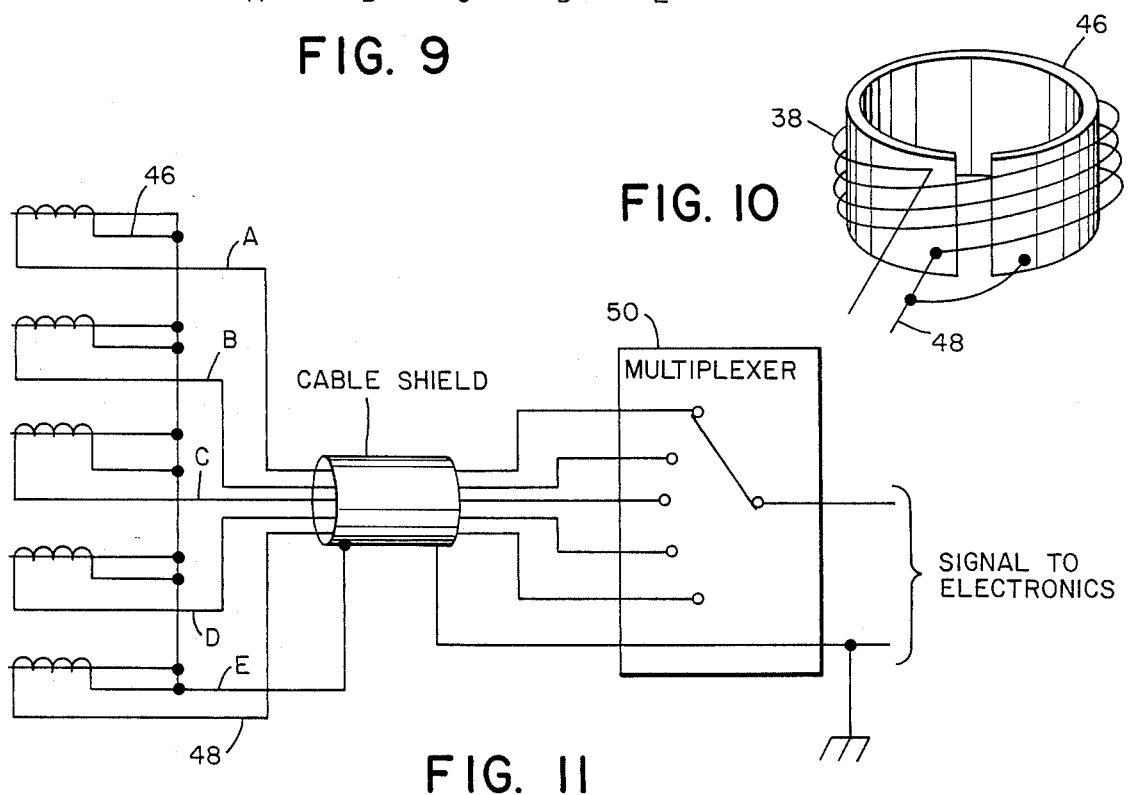
FIG. 10
FIG. 11
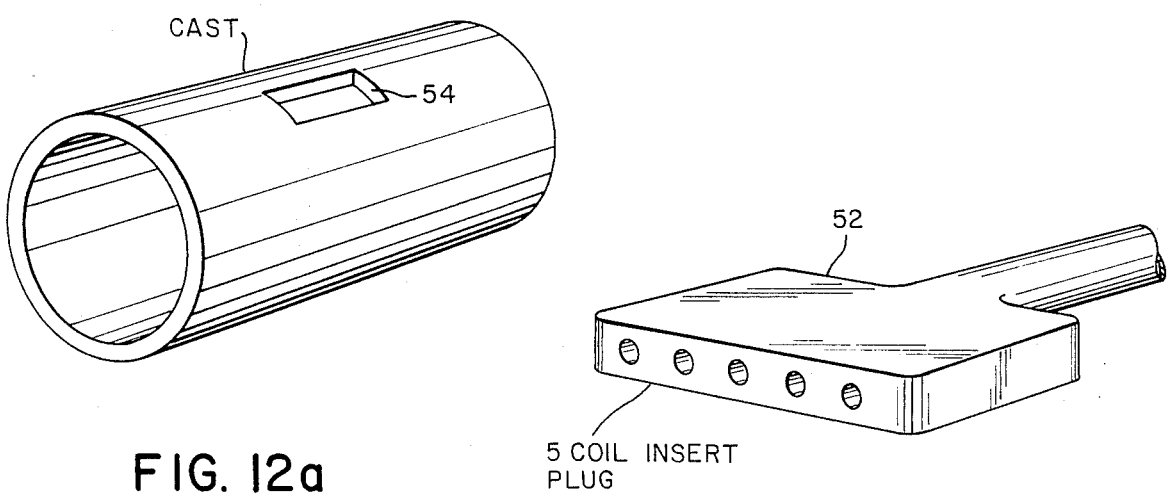
FIG. 12a
FIG. 12b

ELECTROMAGNETIC BONE HEALING SENSOR USING A MULTI-COIL SENSOR ARRAY

STATEMENT OF GOVERNMENTAL INTEREST

The Government has rights in this invention pursuant to Contract No. N00024-85-C-5301 awarded by the Department of the Navy.

REFERENCE TO RELATED CASE

This is a continuation-in-part of a patent application filed on July 11, 1985, Ser. No. 753,824, now U.S. Pat. No. 4,688,580.

BACKGROUND OF THE INVENTION

1. Field of the Invention

The invention relates to a method and apparatus for locating a fracture site in a human or animal bone and for monitoring the mechanical strength at the fracture site during the healing process. More particularly, the invention uses a plurality of electromagnetic fields generated by a multi-coil sensor array to non-invasively measure impedance changes at and about a bone fracture site during the healing process.

2. Description of the Prior Art

Currently the prior art does not teach an effective method or apparatus for measuring non-invasively the mechanical strength of a bone fracture during the healing process. X-ray techniques are of some assistance but fail to quantitatively indicate mechanical strength. In most cases, a physician maintains the broken bone in a cast for what is conservatively a sufficiently long time for mechanical strength to return to the fracture site. However, such a technique is inadequate for certain patients, including the elderly, who have a healing process which proceeds at an unknown rate which is however slower than normal. Similarly, it would be advantageous to have an early removal of a cast so that the patient could return to normal activities. This would be particularly true of athletes who could return to normal professional activities as soon as adequate mechanical strength had returned to the fracture site.

As will be discussed in detail subsequently in this application, Applicants have related the impedance change at a fracture site with changes in mechanical strength during the healing process. To non-invasively detect such an impedance change, Applicants have invented a method and apparatus which uses an electromagnetic field for sensing such an impedance change, at the fracture site. U.S. Pat. No. 3,735,245 entitled "Method and Apparatus for Measuring Fat Content in Animal Tissue Either in Vivo or in Slaughtered and Prepared Form" invented by Wesley H. Harker, teaches that the fat content in meat can be determined by measuring the impedance difference between fat and meat tissue. The Harker apparatus determines gross impedance change and does not provide adequate spatial resolution for the present use. U.S. Pat. No. 4,240,445 teaches the use of an electromagnetic field responsive to the dielectric impedance of water to detect the presence of water in a patient's lungs. However, such an apparatus does not detect the conductivity variations required in the present invention. U.S. Pat. No. 3,789,834 relates to the measurement of body impedance by using a transmitter and receiver and computing transmitted wave impedance from the electrical or magnetic field generated. However, the antenna pickup would receive extraneous noise rendering it inappropriate for the present use. None of the above cited references contemplate measuring the mechanical strength of a bone by measuring the impedance change along a fractured region, and none of the references teach an apparatus capable of specifically detecting such impedance changes.

SUMMARY OF THE INVENTION

The present inventors realized through experimentation that the impedance change at the fractrue site of a bone could be related to the extent of the fracture and to the degree of healing. They discovered that the electrical impedance of the bone at the fracture site increases with the extent of a transverse bone fracture. They further discovered that the conductivity profile along a bone changes in a systematic way during the healing process.

The present inventors also realized that the impedance change at the fracture site and along the bone could be sensed non-invasively using a magnetic field and detecting the change in mutual inductance between the sensor and the body. The basic sensor utilizes a thin or narrow magnetic field coil winding which spatially concentrates the magnetic field and detects the impedance change about the fracture site. As a limb is passed within the proximity of the spatially discrete coil detector, the mutual inductance of the coil is detected and produces a change in the resonant amplitude and resonant frequency of the detection oscillator. The invented apparatus is capable of detecting small variations in impedance changes and quantitatively measuring such changes. The oscillator detector in combination with the magnetic coil is specifically designed to be sensitive to small impedance changes and to reduce polarization effects and background noise which could render such monitoring impossible.

A first novel feature of the invention is the method of detecting a bone fracture by measuring impedance changes at and about the fracture site.

A second novel feature of the invention is a means for non-invasively measuring mechanical strength of a bone fracture during the healing process by quantitatively measuring changes in impedance at and about the fracture site.

A third novel feature of the invention is the use of a coil winding and oscillator detector to detect changes in the impedance at the fracture site by noting changes in resonant frequency and resonant amplitude caused by changes in mutual inductance.

A fourth novel feature of the invention is a coil winding which is specifically designed to provide sufficient spatial resolution so that changes in impedance along a thin fracture site can be observed.

A fifth novel feature of the invention is the use of a coiled winding and an oscillator detector to detect small changes in impedance and which is adapted to quantitatively display such changes in impedance by displaying changes in the resonant frequency and resonant amplitude of the oscillator detector.

A sixth novel feature of the invention is the use of a multi-coil sensor array that can be either mounted in the cast or mounted onto a plug that is inserted through a window in the cast.

BRIEF DESCRIPTION OF THE DRAWINGS

FIG. 9 illustrates a multi-coil sensor array that can be either sutured to a patient's skin or mounted in a cast.

FIG. 10 is an enlarged three-dimenional view of a sensor coil.

FIG. 11 is a schematic drawing of the multi-coil sensor array.

FIGS. 12A and B illustrate an insert plug embodiment of the multi-coil sensor array for insertion through a window of a cast into a position adjacent to the fracture site.

DETAILS OF DESCRIPTION OF THE EMBODIMENT

The present invention is based on the Applicants' discovery that the electrical impedance of the bone at a fracture site increases with the extent of a transverse bone fracture. Further, the healed fracture has a different impedance from the original bone and the impedance change is proportional to the mechanical strength of the bone. The present invention is directed to a non-invasive method and apparatus for measuring the local impedance at the site of the bone fracture.

Figure 1:
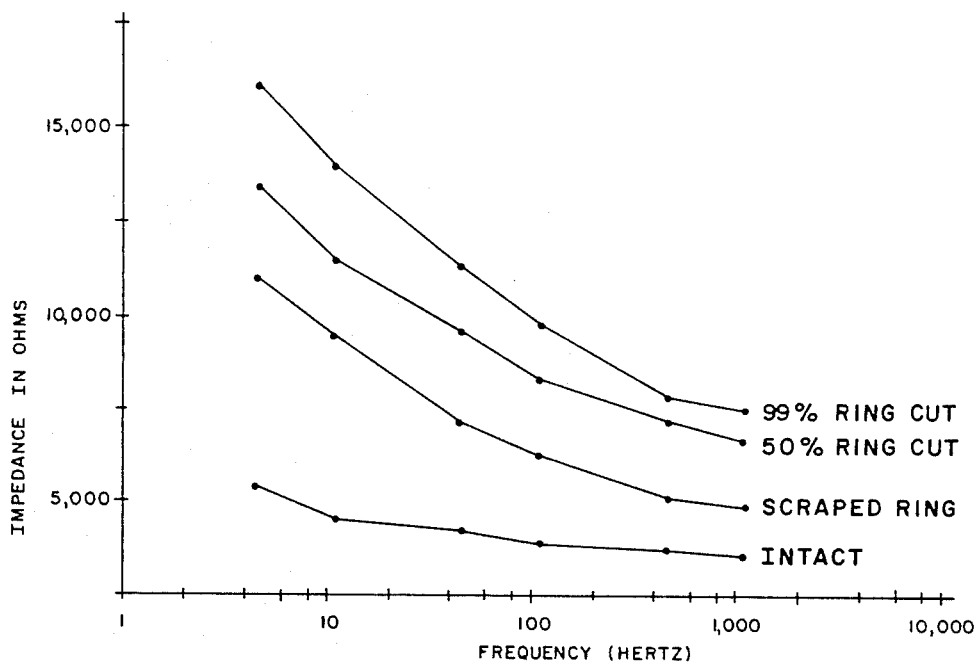
FIG. 1 is a graph showing bone impedance changes of the tibia as a function of frequency and extent of fracture.
Figure 2:
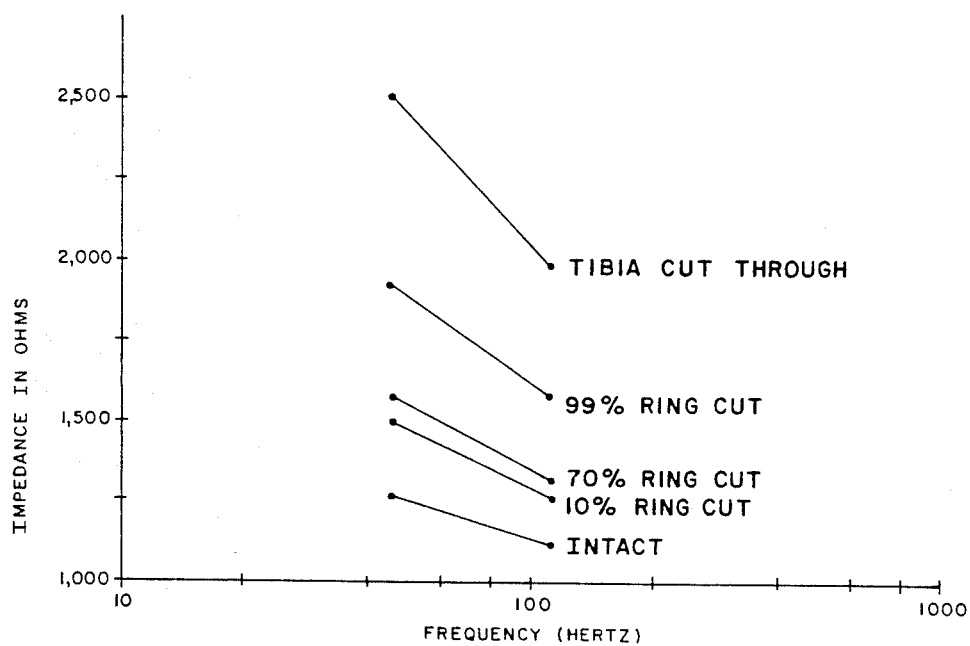
FIG. 2 is a graph showing the bone impedance changes for the tibia, with the fibula attached, as a function of frequency and extent of fracture.

FIGS. 1 and 2 show some of the initial impedance measurements of a fractured cadaver tibia. An initial invasive method was used wherein stainless steel electrodes were installed near both ends of the tibia so that the bone could be made part of a series circuit for measuring both bone impedance and the non-linearities of the impedance as a function of the degree of bone fracture. Transverse ring cuts were made circumferentially around the bone to simulate a bone fracture, and the cut bones were saturated in a saline solution. FIGS. 1 and 2 show that the electrical impedance of the bone increases with the extent of transverse fracture.

Figure 3:
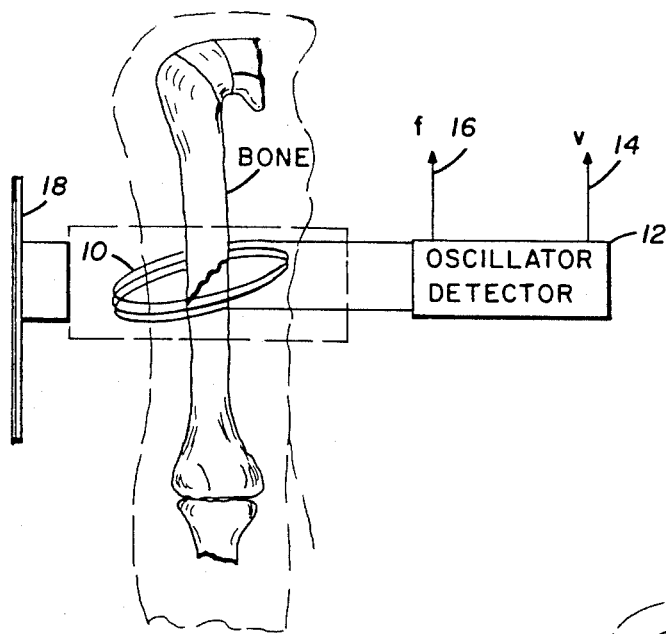
FIG. 3 is a block diagrammatic illustration of the present invention showing the use of a thin coil detector.
Figure 4:
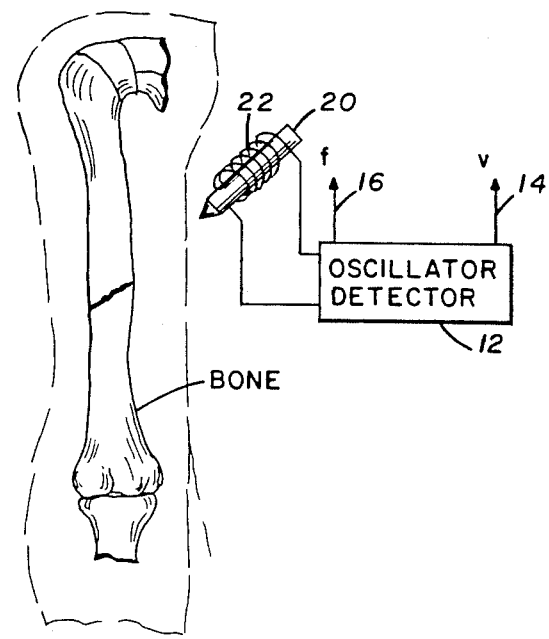
FIG. 4 is a block diagrammatic illustration of the present invention showing a wand magnetic detector which increases spatial resolution of the sensor system.

FIGS. 3 and 4 show a schematic representation of a non-invasive apparatus as taught by the present invention. The basic sensor is a thin or narrow magnetic field coil winding 10 which detects the presence of matter of different electrical productivity. The apparatus uses the same principle as some metal detectors which are used at the airport. As the conducting material passes within the proximity of the coil detector, the mutual inductance of the coil in the electronic circuit changes the frequency of oscillation of the detector circuit. The amount of oscillation is proportional to the value of the electrical conductivity passing through the detector coil. The magnetic field of the coil creates an electric field. The electric field creates induced eddy currents within the conducting bone material. These induced eddy current re-radiate a magnetic signal, which is detected by the detector coil. The amount of magnetic field which is re-radiated is proportional to the amount of eddy current which is induced. The amount of eddy current which is induced is proportional to the electrical conductivity of the bone.

Returning to FIG. 3, a broken limb would be passed through detector coil 10 which non-invasively ascertains the electrical conductivity in that section of the arm contained in the coil. Oscillator detector 12 is connected to the coil 10 and generates an oscillating magnetic signal in the coil. The change in mutual inductance of the coil is picked up by oscillator detector and results in a change in output 16 indicating a frequency change and output 14 indicating a voltage change. The extent of electrical conductivity of the bone is proportional to the degree of the fracture healing. The impedance change that coincides with the fracture healing process will vary from a high impedance of 20K ohms to a lower impedance of 0.01 ohm. Therefore, if a fresh fracture is measured, the electrical impedance is expected to be high; that is, the conductivity will have a low value. As the fracture heals, the electrical impedance will diminish and the electrical conductivity will increase. In this embodiment the detector coil 10 could operably slide on a track 18, so that linear displacement along the bone can be measured.

Alternatively, the embodiment shown in FIG. 4 could be used. In this embodiment coil 20 is wrapped around a magnetic core 22 to concentrate the magnetic flux lines. The slide or wand arrangement (18, 22) is operably moved across the fracture site as outputs (14, 16) are monitored.

It is expected that irradiation caused by the magnetic field will cause no harm to the patient.

Figure 5:
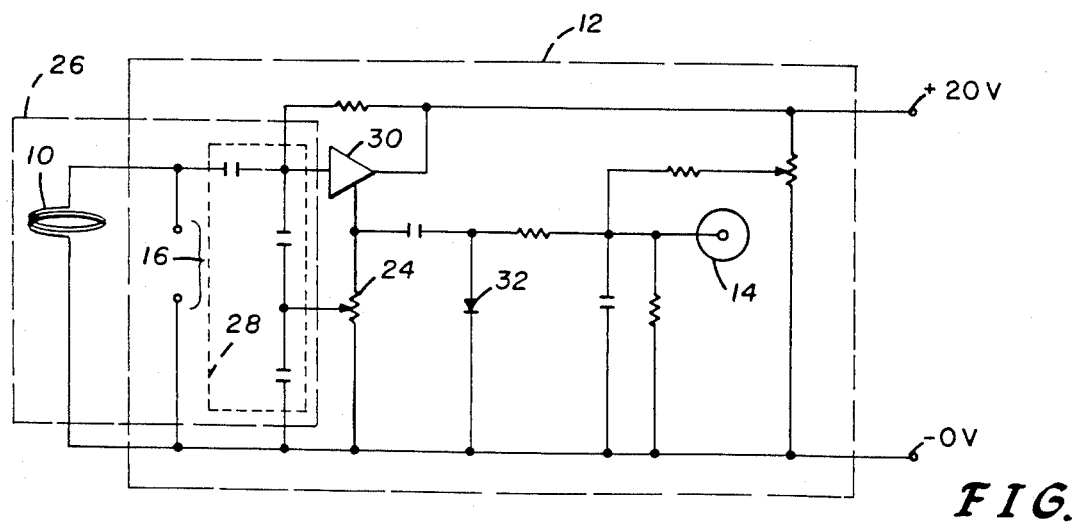
FIG. 5 is a schematic diagram of a typical circuit used in the present invention.

FIG. 5 is a schematic drawing of one possible circuit configuration for oscillator detector 12. Electronically, the circuit represents a marginally stable Colpitts oscillator whose frequency of oscillation is determined by the tank circuit. Although a Hartley-type oscillator, or similar, would work equally well. The potentiometer tap 24 helps to find the proper circuit resistance external to the tank circuit 26 resistance needed for stable oscillation. The tank circuit 26 includes coil 10 and capacitors 28. The transistor 30 with negative feedback provides stable voltage gain. A DC output 14 is extracted from the demodulator diode 32 which reflects the change in oscillator amplitude. The frequency is measured directly off coil 10 at output 16. When a bone is place through coil 10, eddy currents are induced by the time changing magnetic field generally by the coil. The eddy currents in turn produced a secondary, though slight, magnetic field whose associated flux is coupled back to the coil. This produces a change in the coil impedance which changes the resonant amplitude, measured at output 14, and the resonant frequency, measured at output 16, of tank circuit 26. The coil inductances are in the millihenry (mH) range so that resonant frequencies in the hundreds of kHz to several MHz are obtained. In this frequency range, the impedance changes are dominated by conductivity properties and not polarization effects caused by the relative permittivity of the media.

Figure 6:
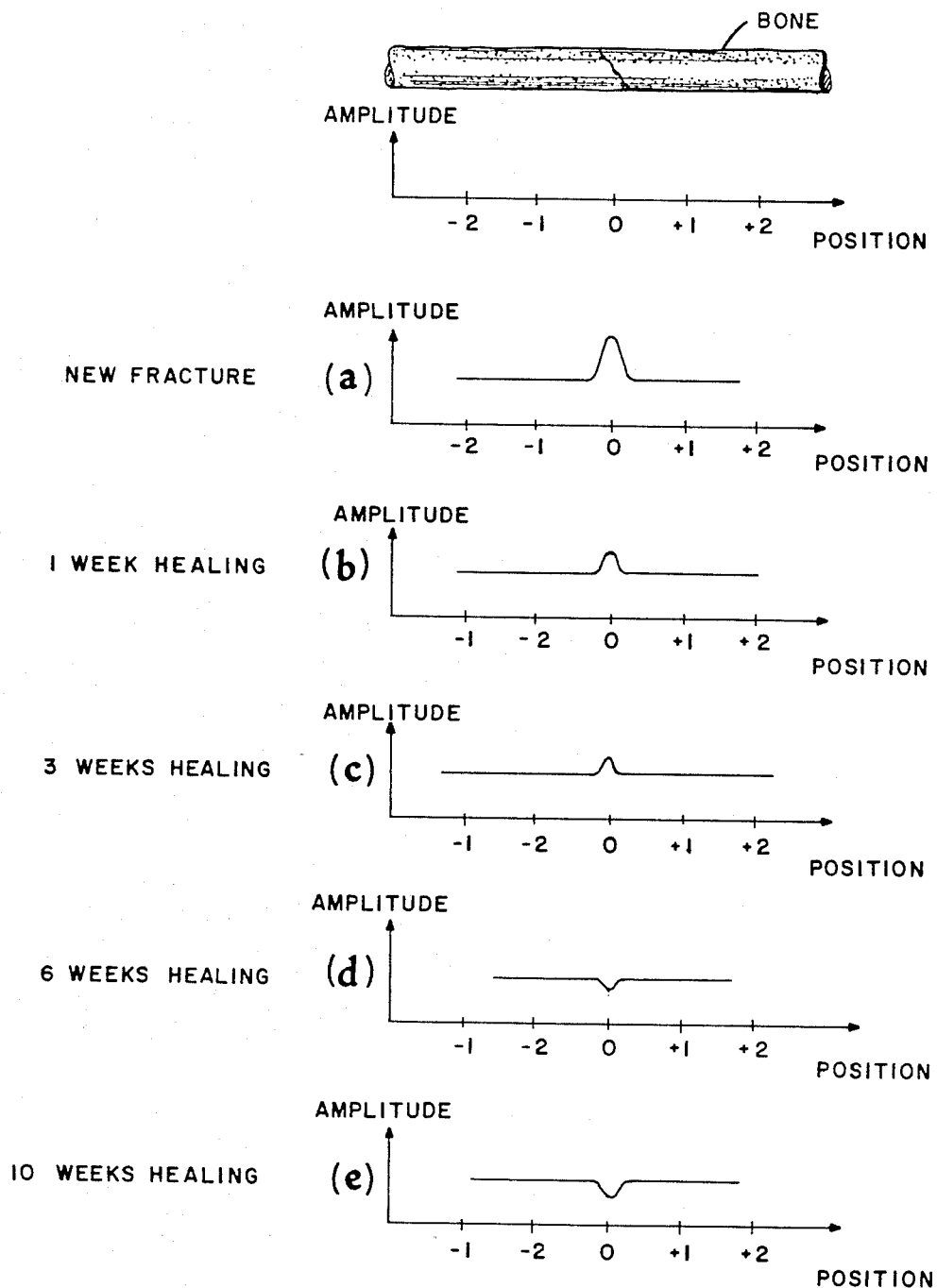
FIG. 6 is a family of graphs showing the change in resonant amplitude as a function of spatial displacement along the bone and as a function of time since the occurrence of the fracture.

FIG. 6 illustrates a change in resonant amplitude, measured at output 14, during the bone healing process. For a fresh fracture (FIG. 6a), the resonant amplitude at the fracture site is high indicating that electrical impedance at the fracture site is also high. As healing progresses (FIG. 6b, c), the resonant amplitude decreases to a value associated with the impedance of unbroken bone. However, as the fracture site strengthens (FIG. 6d, e) a change in polarity in the resonant amplitude occurs.

Figure 7:
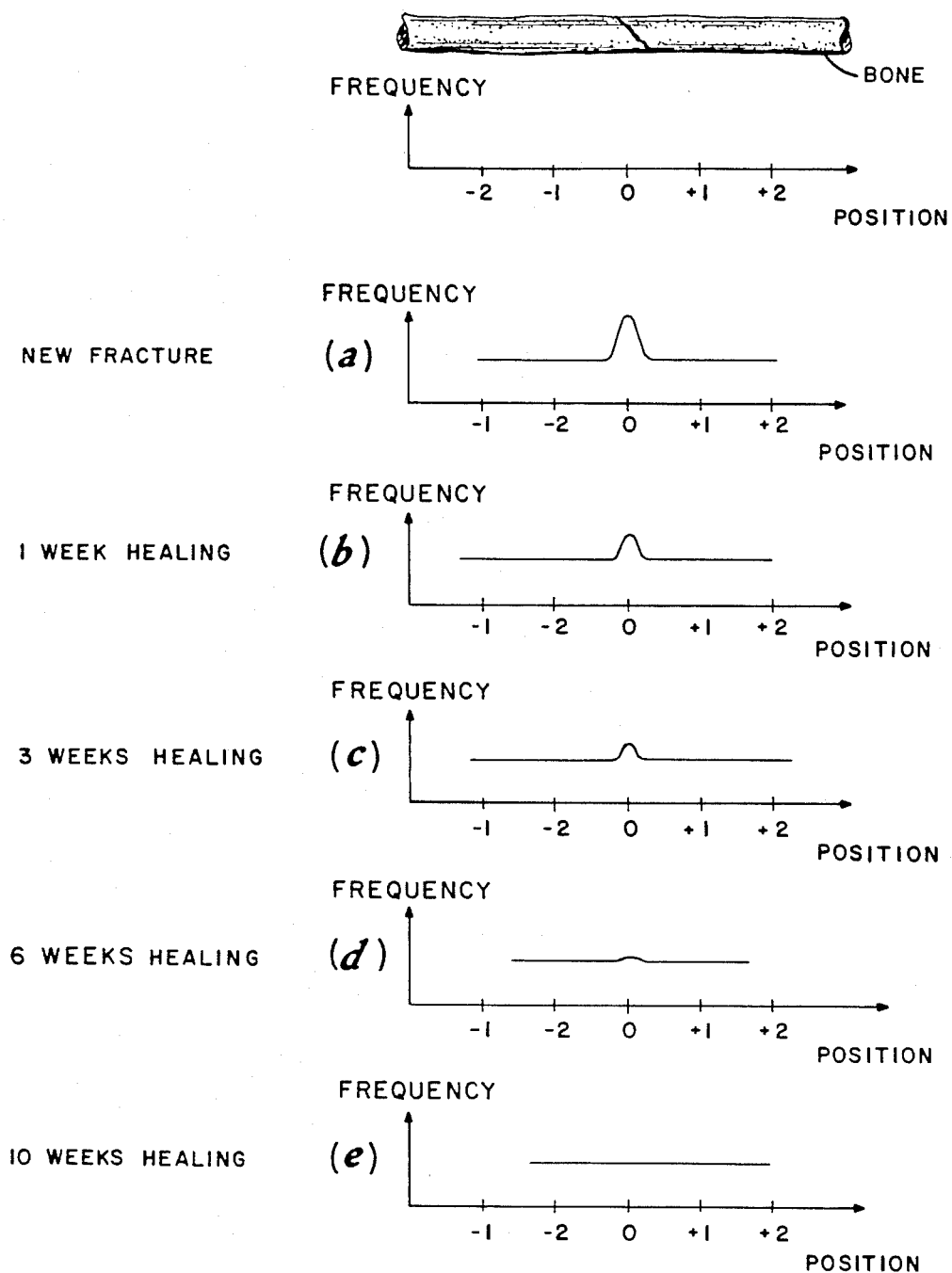
FIG. 7 is a family of graphs showing the change in resonant frequency as a function of spatial displacement along the bone and as a function of time since the occurrence of the fracture.

FIG. 7 illustrates a change in the resonant frequency, measured at output 16 during the bone healing process. For a fresh fracture (FIG. 7, 8), the resonant frequency at the fracture site is high indicating a high electrical impedance. As healing progresses (FIG. 7b–e), the resonant frequency will decrease until it has a value similar to the resonant frequency of unbroken bone.

Figure 8:
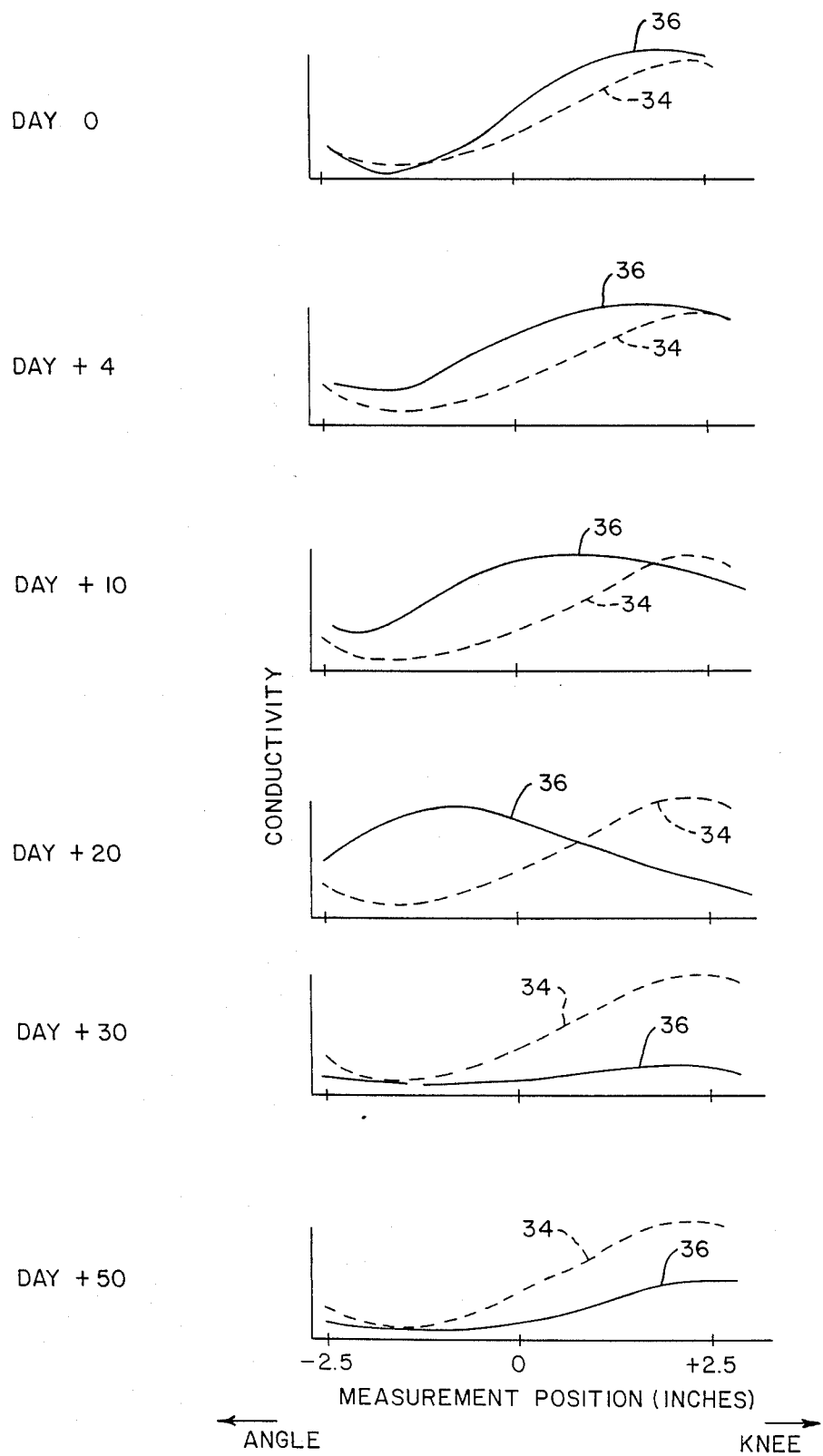
FIG. 8 is a series of graphs showing the conductivity along a bone fracture during the healing process.

FIG. 8 is a series of graphs showing the general conductivity changes along legs during the fracture healing process. Each graph in FIG. 8 is a plot of conductivity (calculated from data) versus measurement position. The results are shown at measurement positions that extend from 2.5 inches below the fracture (toward the ankle) to 2.5 inches above the fracture (toward the knee). The measurement position "0" is directly over the fracture. The graph derived from the fractured leg is noted by the solid line. The results from the normal leg are noted by the dotted line. Six graphs are noted stylizing the results obtained on the day of surgery (day 0) and approximately 4, 10, 20, 30, 50 days after surgery. The data used to generate the general conductivity graphs of FIG. 8 was gathered during animal trials. During the trials a single one-inch diameter air core sensor was used to measure the conductivity along the length of the lower hind leg of a dog. On each dog one hind leg is designated the "normal" or "control" leg (34) since it is measured in its "unaltered" state. The other hind leg is the "broken" or "fractured" leg (36) since this leg is cut apart in a procedure called an osteotomy. This broken leg is casted for the duration of the fracture healing period, which has lasted as long as six months. Periodically, the cast is removed and the 1"air core coil is moved along the broken leg. At measurement stations one-quarter inch apart, data are taken from which the conductivity is calculated.

FIG. 9 illustrates a multi-coil sensor array that can be either sutured to the skin of a patient or sutured or glued into the cast in a position proximate to the fracture site. Center sensor coil "C" should be placed over the fracture site. Each coil 38 is approximately ½" in diameter and is attached to a flexible plastic substrate 40 and attached to the electronics via cable 42. Suture holes 44 were provided to secure the plastic substrate either to the patient's skin or to the cast. Inside each coil sensor is a thin copper shield 46 that is electrically connected to the ground wire of the coil system.

FIG. 10 is a three-dimensional view of the coil 38 and shield 46. Note that the shield 46 is not itself a closed-loop, and that the shield 46 and one side of the coil is connected to the groun wire 48. FIG. 11 is a schematic drawing which better shows how the multi-coil sensor array can be connected to the electronics (see FIG. 5). A common ground wire 48 connects to each coil and the shield 46 associated with each coil. Output wires (A–E) connect to a multiplexer 50 and are input to the processing electronics.

FIGS. 12A and B illustrate how the multi-coil sensor array can be mounted onto a plug 52 that can be inserted through a window 54 in the cast. The window 54 is formed in the cast over the area of the fracture site, and may have a portion that is removed to expose the skin of the fracture site. The insert plug 52 would be inserted through the window 54 and measurements can be taken without removing the coil. This insert plug 52 would enable frequent clinical measurements to be made with the coils in very close proximity (if not in contact) with the skin.

Obviously, many modifications and variations of the present invention are possible in light of the above teachings. It is therefore to be understood that within the scope of the appended claims the invention may be practiced otherwise than is specifically described.

What is claimed is:

1. An apparatus for sensing bone healing, comprising:
an excitation means for sequentially generating a plurality of spatially concentrated oscillating magnetic fields along a bone in the area of a fracture site, whereby eddy currents induced in bone and other biological matter will produce secondary magnetic fluxes which vary in response to the impedance of bone and other biological matter located in each of said spatially concentrated oscillating magnetic fields, wherein said excitation means comprises a plurality of coil means for producing said plurality of spatially concentrated magnetic fields and an oscillator means operably coupled to each of said coil means through a multiplexing means for sequentially connecting each of said means to said oscillator means, and wherein said plurality of coil means are mounted in a plug adapted to be inserted in a window formed in a cast, so as to enable said plug to be inserted through said window into a position in close proximity to the patient's skin; and,
a processing means for detecting said secondary magnetic fluxes and for processing and displaying information indicating the local impedance along the bone.

2. An apparatus for sensing bone healing, comprising:
an excitation means for sequentially generating a plurality of spatially concentrated oscillating magnetic fields along a bone in the area of a fracture site, whereby eddy currents induced in bone and other biological matter will produce secondary magnetic fluxes which vary in response to the impedance of bone and other biological matter located in each of said spatially concentrated oscillating magnetic fields, wherein said excitation means comprises a plurality of coil means for producing said plurality of spatially concentrated magnetic fields and an oscillator means operably coupled to each of said coil means through a multiplexing means for sequentially connecting each of said coil means to said oscillator means;
a processing means for detecting said secondary magnetic fluxes and for processing and displaying information indicating the local impedance along the bone; and,
a cast having a window adapted to be positioned in an area above the fracture site and, wherein said excitation means further includes a plug, containing said plurality of coil means, removably inserted into said window, said coil means being mounted on said plug so that said coil means can be placed in close proximity to the fracture site.

* * * * *

UNITED STATES PATENT AND TRADEMARK OFFICE
CERTIFICATE OF CORRECTION

PATENT NO.   :   4,860,756
DATED        :   August 29, 1989
INVENTOR(S)  :   Ko et al.

It is certified that error appears in the above—identified patent and that said Letters Patent is hereby corrected as shown below:

In the claims:

Column 6, line 31, after "said" insert -- coil --.

Signed and Sealed this

Seventeenth Day of July, 1990

Attest:

HARRY F. MANBECK, JR.

Attesting Officer

Commissioner of Patents and Trademarks